(12) United States Patent
Thielman et al.

(10) Patent No.: US 11,241,815 B2
(45) Date of Patent: Feb. 8, 2022

(54) DIE FOR CONTINUOUSLY MANUFACTURING TEXTURED SURFACES AND METHODS OF MANUFACTURE THEREOF

(71) Applicants: SHARKLET TECHNOLOGIES, INC., Aurora, CO (US); COOK MEDICAL TECHNOLOGIES LLC, Bloomington, IN (US)

(72) Inventors: Walter S. Thielman, Palatine, IL (US); Ryan E. Stoneberg, Wheeling, IL (US); Wade Gyure, Crown Point, IN (US)

(73) Assignees: SHARKLET TECHNOLOGIES, INC., Aurora, CO (US); COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 16/332,918

(22) PCT Filed: Sep. 20, 2017

(86) PCT No.: PCT/US2017/052434
§ 371 (c)(1),
(2) Date: Mar. 13, 2019

(87) PCT Pub. No.: WO2018/057582
PCT Pub. Date: Mar. 29, 2018

(65) Prior Publication Data
US 2019/0224903 A1 Jul. 25, 2019

Related U.S. Application Data

(60) Provisional application No. 62/396,979, filed on Sep. 20, 2016.

(51) Int. Cl.
*B29C 48/30* (2019.01)
*B29C 48/25* (2019.01)
(Continued)

(52) U.S. Cl.
CPC ..... *B29C 48/3001* (2019.02); *A61M 25/0009* (2013.01); *B29C 48/10* (2019.02);
(Continued)

(58) Field of Classification Search
CPC ......... B29C 48/30; B29C 48/09; B29C 48/10; B29C 48/40; B29C 48/002;
(Continued)

(56) References Cited

U.S. PATENT DOCUMENTS 3,820,374 A * 6/1974 Braeuninger ......... B29C 48/475
72/265
4,698,196 A * 10/1987 Fabian .................... B29C 55/26
264/565
(Continued)

FOREIGN PATENT DOCUMENTS

| EP | 0015312 A1 | 9/1980 |
| EP | 2535077 A2 | 12/2012 |
| WO | 2012037384 A2 | 3/2012 |

OTHER PUBLICATIONS

International Search Report for International Application No. PCT/US2017/052434 ; International Filing Date Sep. 20, 2017; dated Nov. 29, 2017; 5 pages.
(Continued)

*Primary Examiner* — Joseph S Del Sole
*Assistant Examiner* — Baileigh Kate Darnell
(74) *Attorney, Agent, or Firm* — Cantor Colburn LLP

(57) ABSTRACT

Disclosed herein is a die assembly comprising a first attachment block having a passage, an inlet port and an exit port; where the passage is operative to transport a molten material from the inlet port to the outlet port; a die; and a conduit; where the conduit comprises a passage that is operative to transport the molten material from the first attachment block to an entry port of the die; where the die comprises a first (Continued)

outer tube; and an extrusion pin that comprises a post and fins; where the extrusion pin is located in the first outer tube using the fins and where the post extends from the fins in a direction away from the entry port of the die; and where the post comprises one or more passages; where at least of these passages open to the atmosphere to provide for pressure equalization; and a travelling template; the template being operative to contact an extrudate that emanates from the die and to transfer a texture to a surface of the extrudate by virtue of pressure applied by a guide tube to the extrudate via the travelling template.

21 Claims, 14 Drawing Sheets

(51) Int. Cl.
  *B29C 48/09* (2019.01)
  *B29C 48/00* (2019.01)
  *B29C 59/00* (2006.01)
  *A61M 25/00* (2006.01)
  *B29C 48/10* (2019.01)
  *B29C 48/40* (2019.01)

(52) U.S. Cl.
  CPC .......... *B29C 48/2566* (2019.02); *B29C 48/40* (2019.02); *B29C 48/002* (2019.02); *B29C 48/09* (2019.02); *B29C 59/00* (2013.01)

(58) Field of Classification Search
  CPC . B29C 48/2566; B29C 48/3001; B29C 59/00; B29C 59/021; A61M 25/0009
  See application file for complete search history.

(56) References Cited

U.S. PATENT DOCUMENTS

| | | | |
|---|---|---|---|
| 5,792,486 A * | 8/1998 | Hsu | B29C 48/325 |
| | | | 425/192 R |
| 6,616,882 B1 | 9/2003 | Lidgett | |
| 9,399,113 B2 * | 7/2016 | Sandford | B29C 48/13 |
| 9,937,655 B2 * | 4/2018 | Chung | A61M 25/0013 |
| 2005/0260374 A1 | 11/2005 | Anand et al. | |
| 2010/0119755 A1 | 5/2010 | Chung | |
| 2012/0319325 A1 | 12/2012 | Chung et al. | |
| 2013/0079753 A1 * | 3/2013 | Sandford | A61M 39/08 |
| | | | 604/525 |
| 2013/0184686 A1 * | 7/2013 | Sandford | B29C 48/33 |
| | | | 604/526 |
| 2014/0052108 A1 | 2/2014 | De Kock et al. | |
| 2015/0342725 A1 | 12/2015 | Cuevas et al. | |
| 2016/0123846 A1 | 5/2016 | Magin et al. | |
| 2017/0152338 A1 | 6/2017 | Brennan et al. | |
| 2017/0216543 A1 | 8/2017 | Magin et al. | |
| 2018/0078423 A1 | 3/2018 | Magin et al. | |
| 2018/0171157 A1 | 6/2018 | Magin et al. | |
| 2018/0214600 A1 | 8/2018 | Magin et al. | |
| 2019/0161627 A1 | 5/2019 | Brennan et al. | |
| 2019/0202109 A1 | 7/2019 | Stoneberg et al. | |
| 2019/0291308 A1 | 9/2019 | Harvey et al. | |

OTHER PUBLICATIONS

Written Opinion for International Application No. PCT/US2017/052434 ; International Filing Date: Sep. 20, 2017; dated Nov. 29, 2017; 8 pages.
U.S. Appl. No. 16/333,027, filed Mar. 13, 2019.
Non-Provisional U.S. Appl. No. 16/346,957, filed May 2, 2019.
Extended European Search Report for EP Application No. 17853786.6; dated May 7, 2020 (8 pages).

* cited by examiner

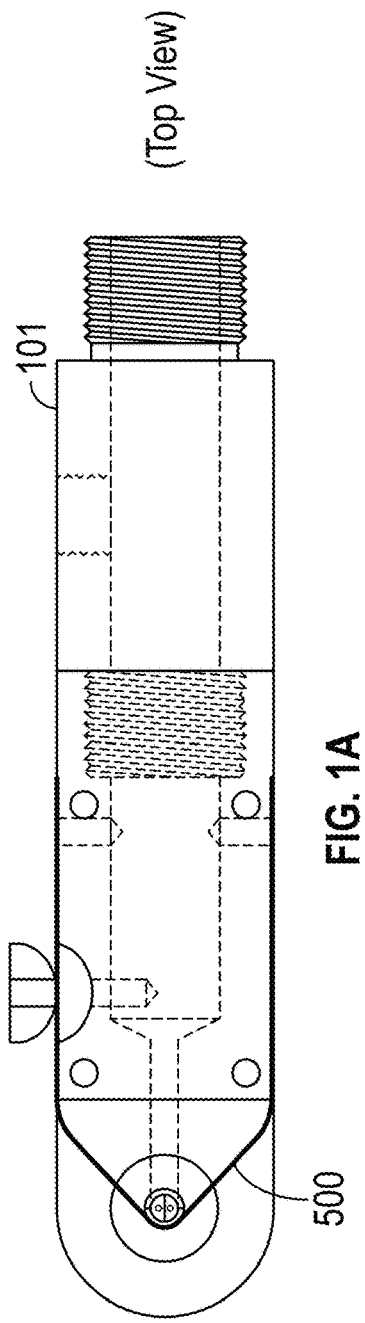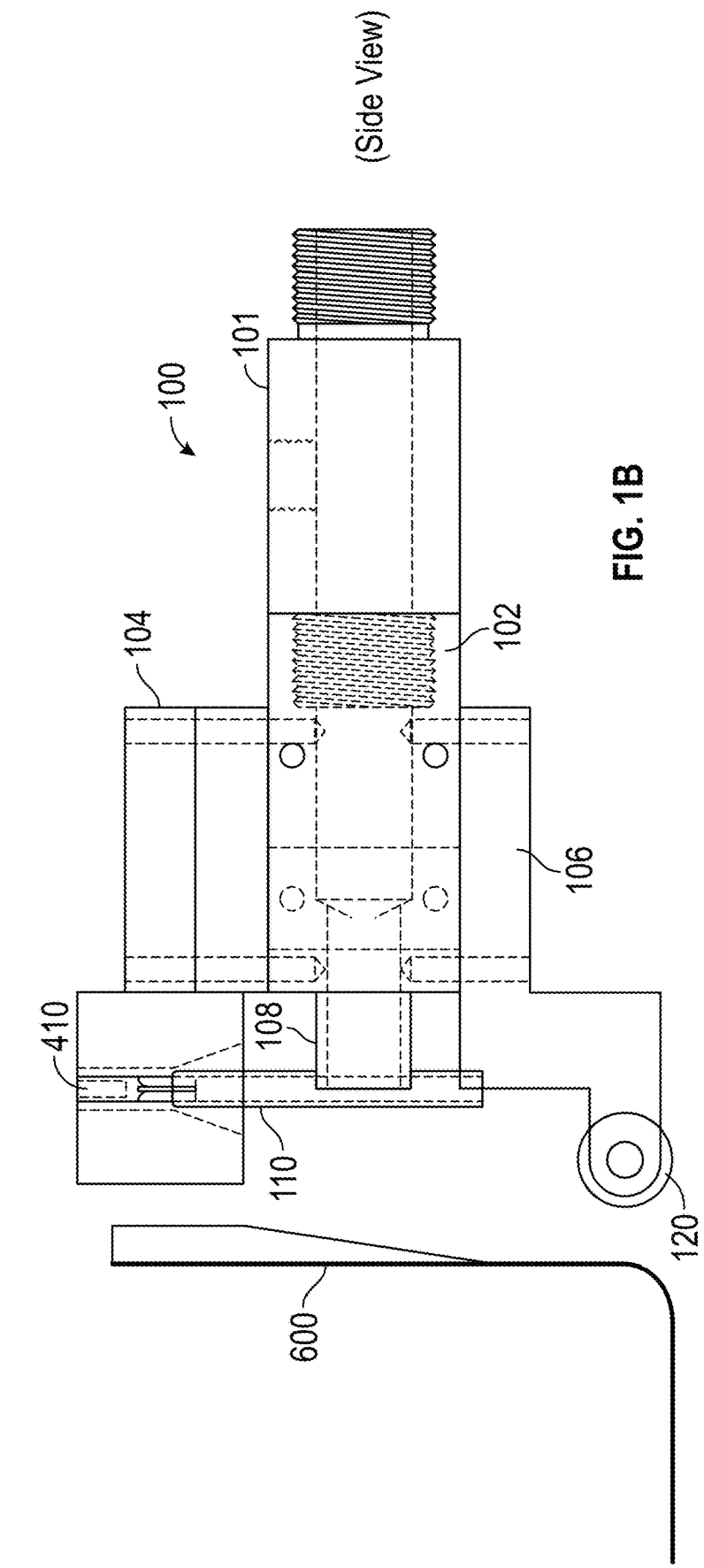
FIG. 1A (Top View)
FIG. 1B (Side View)

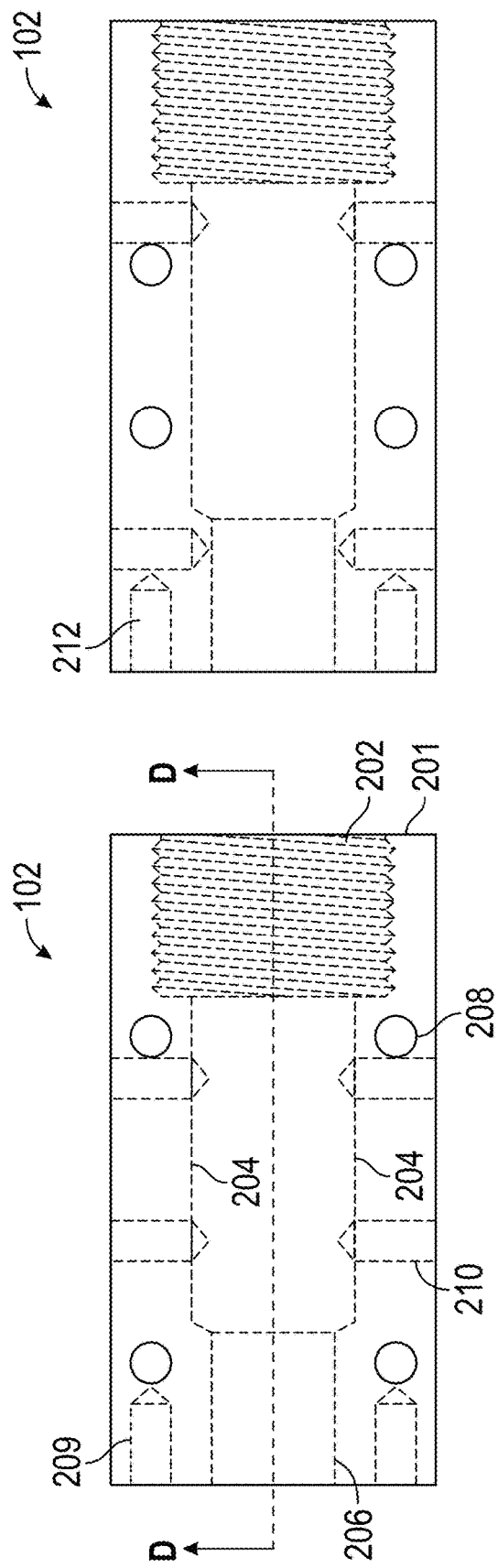
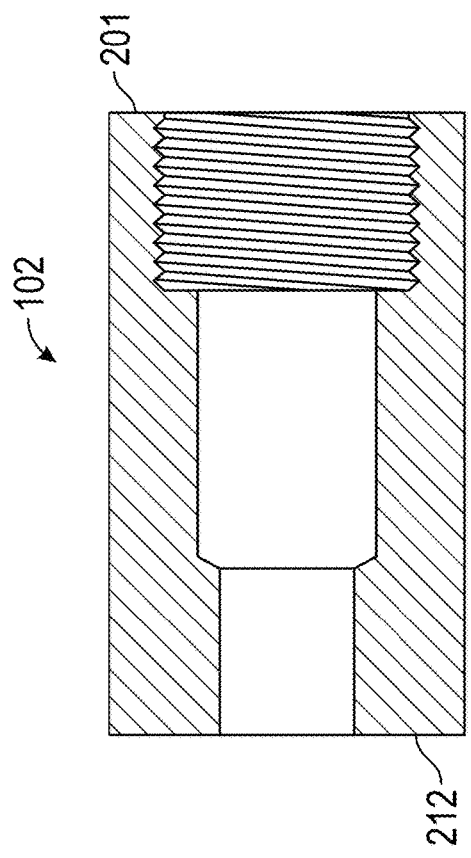
FIG. 2A (Side View)
FIG. 2B (Top View)
FIG. 2C (Section D-D)

FIG. 2D (Front View)

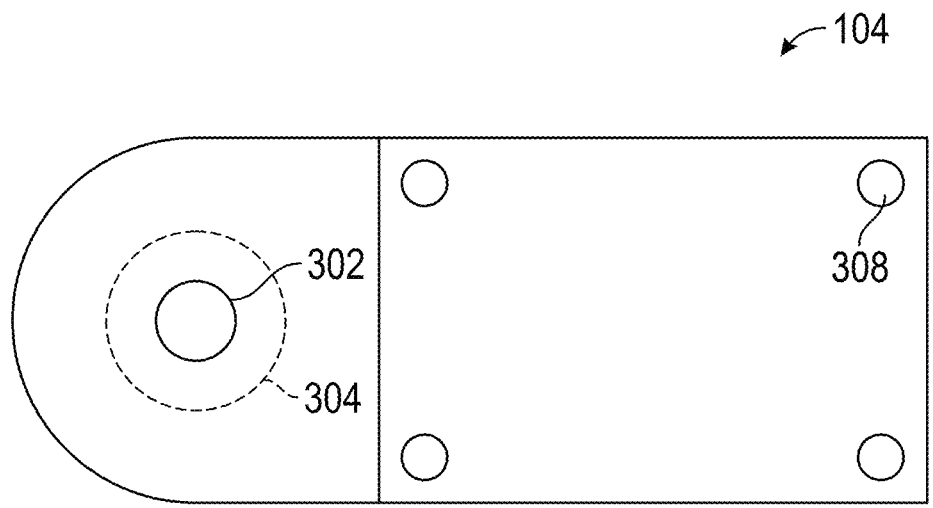
FIG. 3A (Top View)
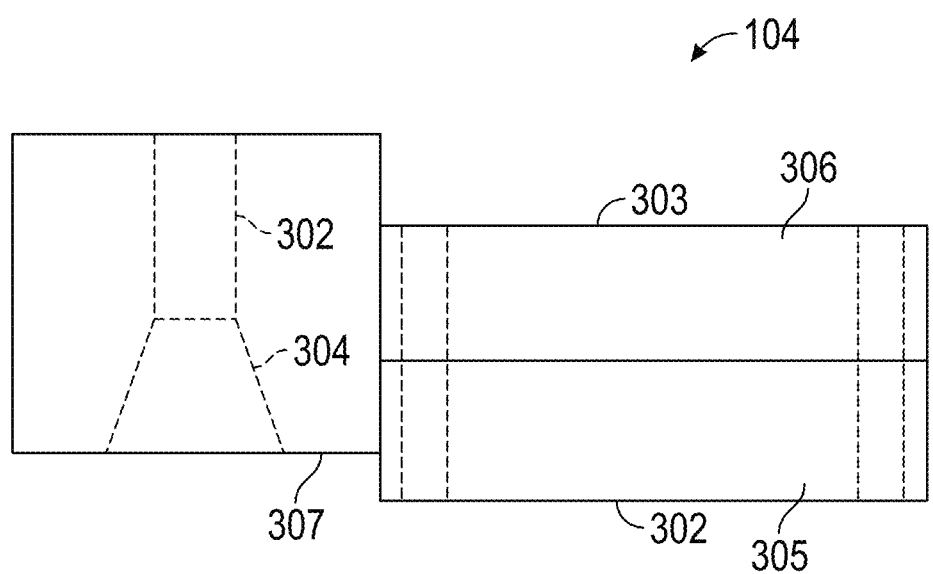
FIG. 3B (Side View)

FIG. 3C (Front View)

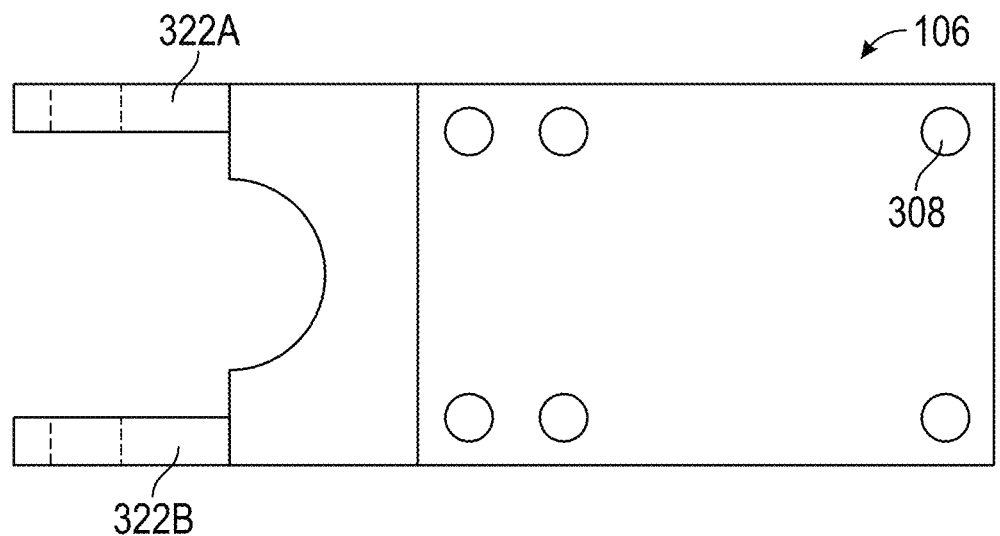
FIG. 4A (Top View)
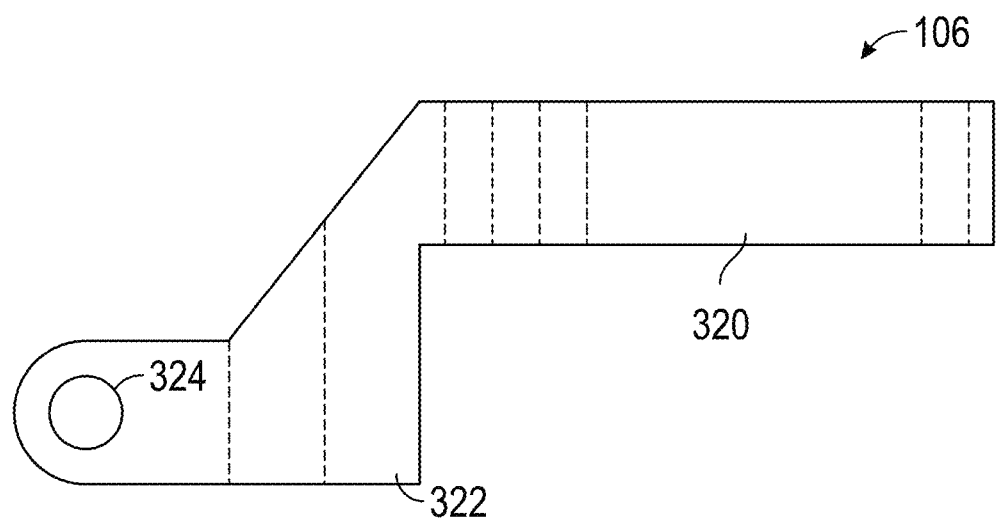
FIG. 4B (Side View)

FIG. 4C (Front View)

FIG. 5A (Top View)

FIG. 5B (Side View)

FIG. 5C (Front View)

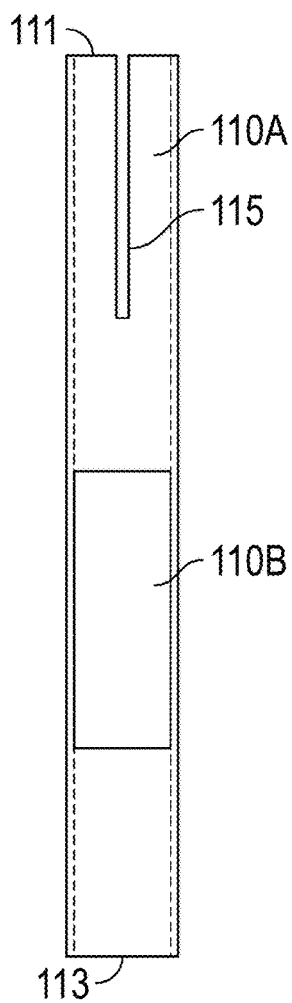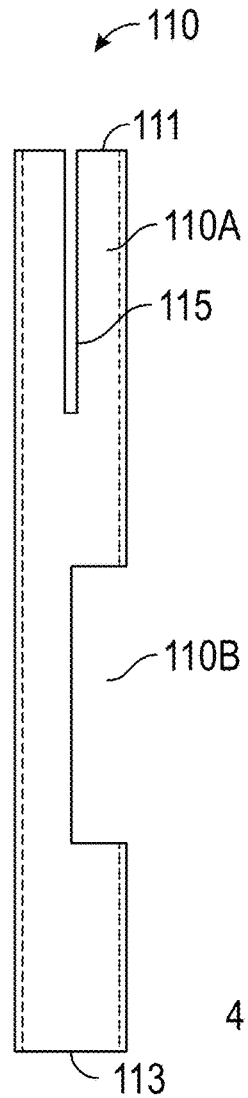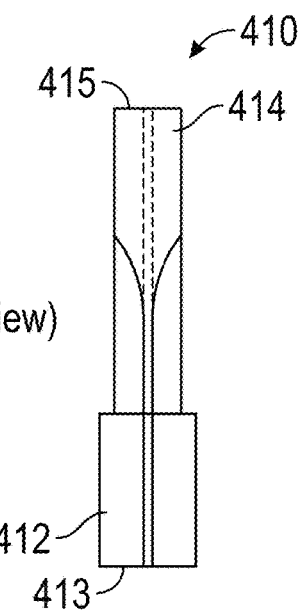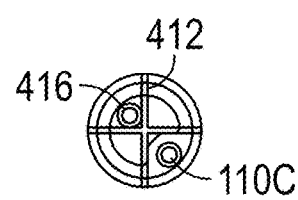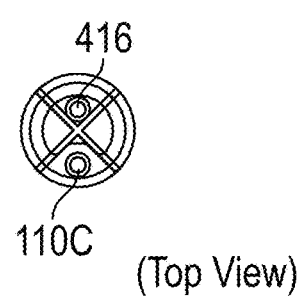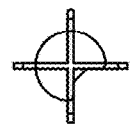
FIG. 6A
FIG. 6B
FIG. 6C
FIG. 6D

DIE FOR CONTINUOUSLY MANUFACTURING TEXTURED SURFACES AND METHODS OF MANUFACTURE THEREOF

CROSS REFERENCE TO RELATED APPLICATIONS

This application is a National Stage application of PCT/US2017/052434, filed Sep. 20, 2017, which claims the benefit of U.S. Provisional Application No. 62/396,979, filed Sep. 20, 2016, both of which are incorporated by reference in their entirety herein.

BACKGROUND

Disclosed herein is a die for manufacturing catheters. More specifically, disclosed herein is a die that permits texturing outer surfaces of an elastomer while creating tubular pathways on the inside that permit the transfer of fluids to a patient.

Catheters are often used for inserting prosthetics into the body of a patient, for transferring fluids to various points in a body, or for removing fluids from various points in a body. Because catheters traverse various parts of the body, bacteria from one part of the body can be transferred to other parts of the body. Additionally, bacteria from outside the body can be transferred to various parts inside the body. It is desirable to prevent this bacterial transfer.

Surfaces that have patterns and other forms of texturing (hereinafter "texturing") can be advantageously used to minimize the adhesion of living organisms and other forms of non-living matter (e.g., ice, dust, dirt, and the like) to the surface. The texturing can have dimensions that are selected to specifically prevent the adhesion of specific living organisms or non-living matter on the surface, while at the same time encouraging the growth of other organisms or the adhesion of other types of non-living matter to the surface.

For example, in order to prevent the growth of certain types of living organisms the dimensions of the texturing may have to be in the nanometer or in the micrometer range, while for preventing the growth of certain other types of organisms, the dimensions of the texturing may have to be in the millimeter or centimeter range. In another example, in order to facilitate the growth of certain types of living organisms the dimensions of the texturing may have to be in the nanometer or in the micrometer range, while for facilitating the growth of certain other types of organisms, the dimensions of the texturing may have to be in the millimeter or centimeter range. Reproducing this texturing on surfaces that are large in size (e.g., of the area of several square centimeters) or on surfaces that have a complex shape (e.g., a non-planar surface that is circular or spherical) is difficult.

In order to traverse and reach various parts of the body, catheters are generally manufactured from flexible materials that have tubular pathways inside them. The tubular pathways allow for the manipulation of prosthetics inside the body. They also allow for fluid transfer to and from the body. This means that the catheter is generally manufactured from a flexible material (e.g., an elastomer). Manufacturing a catheter with multiple tubular pathways from a flexible material while at the same time disposing texturing on an outside surface of the catheter requires a special die.

SUMMARY

Disclosed herein is a die assembly comprising a first attachment block having a passage, an inlet port and an exit port; where the passage is operative to transport a molten material from the inlet port to the outlet port; a die; and a conduit; where the conduit comprises a passage that is operative to transport the molten material from the first attachment block to an entry port of the die; where the die comprises a first outer tube; and an extrusion pin that comprises a post and fins; where the extrusion pin is located in the first outer tube using the fins and where the post extends from the fins in a direction away from the entry port of the die; and where the post comprises one or more passages; with at least one of these passages being open to the atmosphere to provide for pressure equalization; and a travelling template; the template being operative to contact an extrudate that emanates from the die and to transfer a texture to a surface of the extrudate by virtue of pressure applied by a guide tube to the extrudate via the travelling template.

Disclosed herein too is a method comprising discharging to a die assembly an extrudate; where the die assembly comprises a first attachment block having a passage, an inlet port and an exit port; where the passage is operative to transport a molten material from the inlet port to the outlet port; a die; and a conduit; where the conduit comprises a passage that is operative to transport the molten material from the first attachment block to an entry port of the die; where the die comprises a first outer tube; and an extrusion pin that comprises a post and fins; where the extrusion pin is located in the first outer tube using the fins and where the post extends from the fins in a direction away from the entry port of the die; and where the post comprises one or more passages; with at least one of these passages being open to the atmosphere to provide for pressure equalization; and a travelling template; contacting the extrudate with the template; and transferring a texture to a surface of the extrudate by virtue of pressure applied by a guide tube to the extrudate via the travelling template.

BRIEF DESCRIPTION OF THE FIGURES

FIG. 1A is a top view of the die assembly;
FIG. 1B is a side view of the die assembly;
FIG. 2A depicts a side view of the first attachment block;
FIG. 2B depicts the top view of the first attachment block;
FIG. 2C is a sectional view of the first attachment block taken along section D-D of the FIG. 2A;
FIG. 2D is a front view of the first attachment block;
FIG. 3A depicts the top view of the first support;
FIG. 3B depicts the side view of the first support;
FIG. 3C depicts the front view of the first support;
FIG. 4A depicts the top view of the second support;
FIG. 4B depicts a side view of the second support;
FIG. 4C depicts a front view of the second support.

FIG. 5A depicts a top view of the conduit that facilitates transmission of the molten polymer from the first attachment block to the die;

FIG. 5B depicts a top view of the conduit that facilitates transmission of the molten polymer from the first attachment block to the die;

FIG. 5C depicts a side view of the conduit that facilitates transmission of the molten polymer from the first attachment block to the die;

FIG. 6A depicts a front and a side view of the die;

FIG. 6B depicts a side view of the extrusion pin;

FIG. 6C depicts another side view of the extrusion pin;

FIG. 6D depicts a top view of the extrusion pin in the die;

DETAILED DESCRIPTION

Figure 1C:
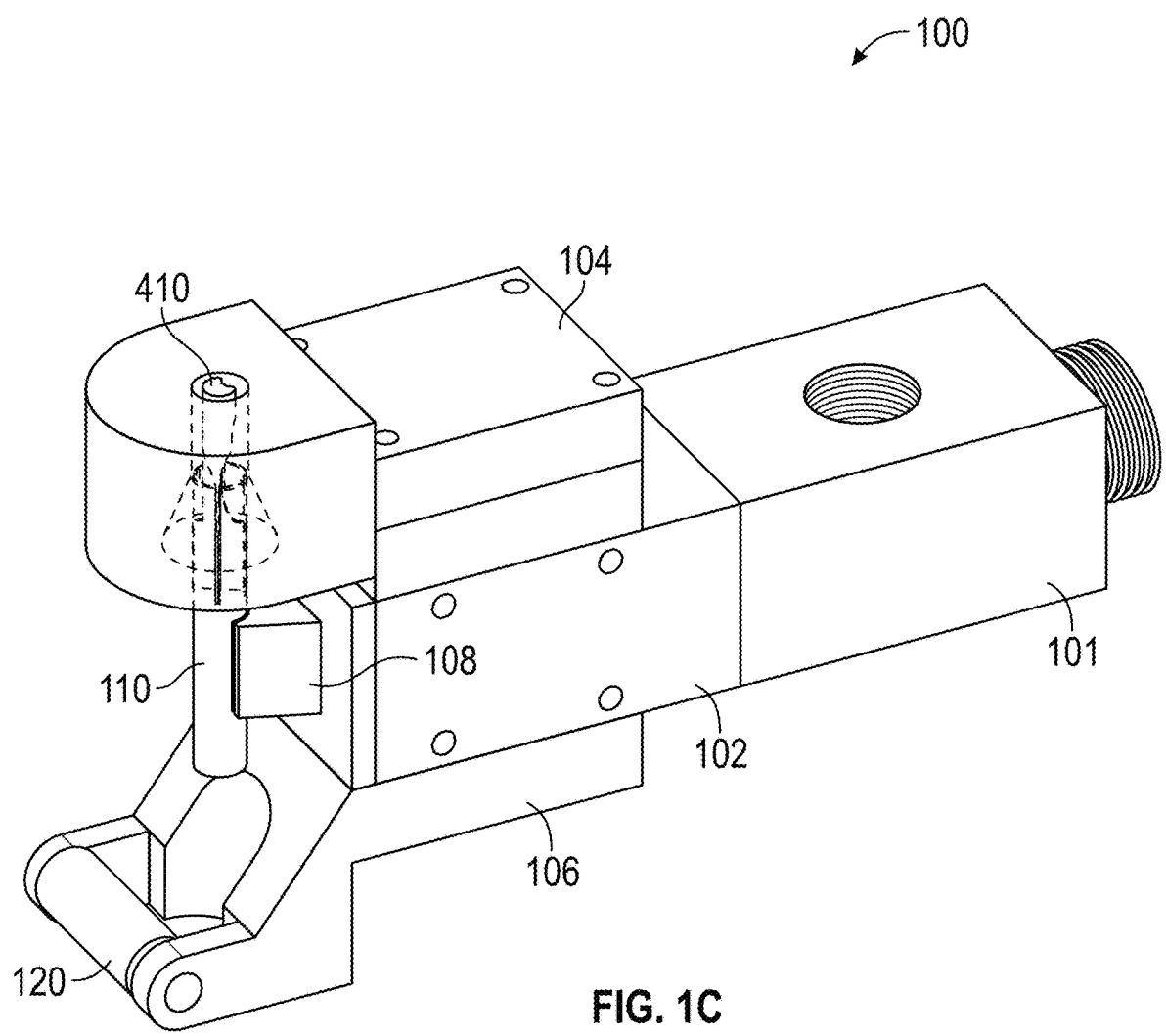
FIG. 1C is a perspective view of the die assembly without the template.

Disclosed herein is a die that can be affixed to an exit of an extruder to produce an article (e.g., an elongated article such as a flexible conduit) that has a plurality of internal passages that traverse its entire length and that has a texture on its entire outer surface. In an embodiment, the die can be used to produce conduits (such as, for example, catheters) that have an outside diameter of at least 1 millimeter (mm). The maximum outside diameter of the conduit can be greater than or equal to 2 mm, preferably greater than or equal to 10 mm, and more preferably greater than or equal to 20 mm. In short, the outside diameter of the conduit can be small.

The die is advantageous in that it permits transferring a pattern to an outer surface of the article in a single pass. In an embodiment, the construction of the die permits a pattern to be transferred to an entire outer surface (the entire outer surface along the entire length) of an elongated article such as a catheter in a single pass through the die. The texture can also be transferred to portions of the elongated article during a single pass through the die. The article is generally manufactured from an elastomer that is very flexible during the manufacturing process and that would be difficult to control (in such a manner as to texture it during the manufacturing process) using a regular die.

In an embodiment, the article comprises elastomers that have an elastic modulus of between 10 kPa and 3 GPa. The texture may have average roughness factor (R) of from 4 to 50 and is distributed on a portion or on the entire surface of the article manufactured in the die in a single pass through the die. In a preferred embodiment, the article does not have to be subjected to more than one pass through the die for purposes of texturing the entire outer surface. It may be reprocessed using the die for other purposes if desired.

The die is a part of a die assembly, details of which are provided below. The die comprises an outer tube having an entry port for permitting an inflow of a polymeric material. The outer tube has slots into which is inserted an extrusion pin having fins that serve as locating elements. The extrusion pin comprises a post onto which the fins are attached. The post has a passage into which is attached a tube that serves as a vent during the extrusion process. The vent allows for pressure equalization in the extruded article which prevents it from collapsing due to the creation of a lower pressure inside the extruded article. The die can also have other tubes located in it to facilitate the inclusion of a radio-opaque material such as barium in the walls of the extruded article. The presence of the radio opaque material in the elongated article permits the location of the article to be tracked when it is inserted into the body of a living being.

During manufacturing, the extrudate (received from the extruder via a die assembly) is transported between the outer tube and the post to form an article onto which the texture is then imparted as it traverses a guide tube located in the die assembly. The texture is imparted via a template which will be described later.

The die in conjunction with the die assembly is therefore capable of imparting a texture to the article as well as of creating passages through the length of the article during a single pass of the polymeric material through the die. The passages may be created through a portion of the length of the article or through the entire length of the article in a single pass.

With reference now to the FIGS. 1A and 1B, a die assembly 100 comprises a first attachment block 102 that can be reversibly affixed to a mouth of the extruder (not shown), a first support 104, a second support 106 that is oppposedly disposed to the first support 103, and a die 110 that is in communication with the first attachment block 102 and the first support 104. The FIG. 1A is a top view of the die assembly 100, while the FIG. 1B is a side view of the die assembly 100. The die 110 is in communication with the first attachment block 102 via a conduit 108 that is operative to facilitate transport a polymeric material to the die 110 from the extruder. The polymeric material may be extruded through the die 110 to form an article (e.g., an elongated article such as a conduit) having a plurality of internal passages that traverse the entire length of the conduit. The die 110 contains an extrusion pin 410 that facilitates the formation of the passages throughout the length of the conduit. The second support has a feed roller 120 that supplies a template (not shown) having the image of a texture disposed on it. When a template 600, e.g. a traveling template contacts an extruded article it transfers the image of the texture to the extruded article. The template 600 is transported via feed roller 120 to contact an outer surface of the die 110 (See FIG. 1E). The template 600 contacts the extrudate (not shown) as it emerges from the die 110 and imprints its texture on the extrudate as the template and the extrudate travel through the guide tube. The template 600 is a moving template that travels along with the extrudate. The travelling template 600 is detailed later in the text. An optional strap 500 secures the die 110 to the first attachment block 102 via a conduit 108. An optional extension conduit 101 may be used to establish contact between the die assembly 100 and the extruder (not shown).

FIG. 1C is a perspective view of the die assembly without the template 600 mounted on the feed roller 120 and contacting the die 110. In the FIG. 1C the extrusion pin 410 is mounted in the die 110. This will be discussed in detail later in the FIGS. 6A-6E.

Figure 1D:
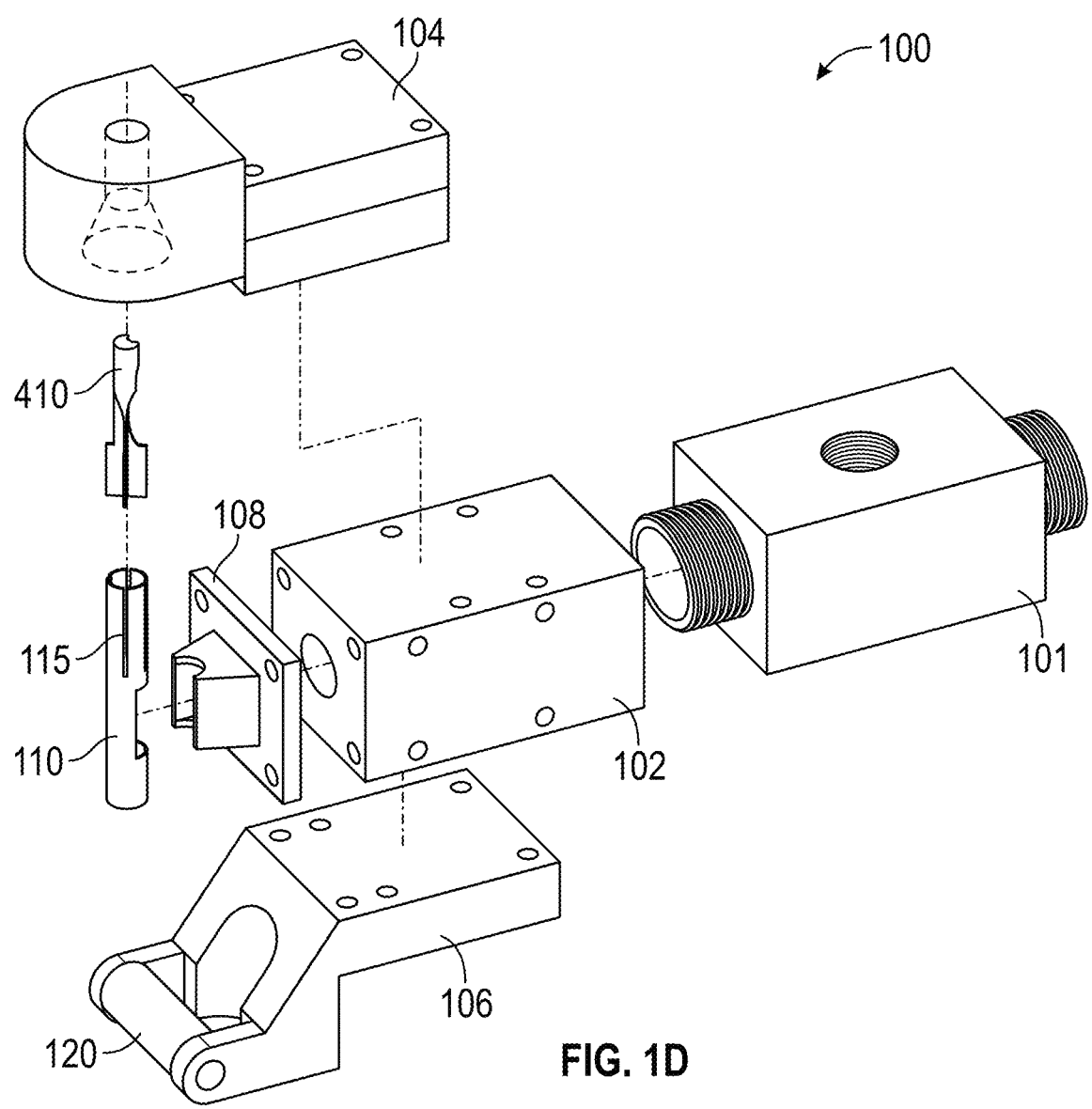
FIG. 1D is a blown-up perspective view of the die assembly without the template. It depicts how the various parts are brought together to manufacture the die assembly.

The FIG. 1D is a blow-up of the die assembly 100 with the various parts separated from each other. The extrusion pin 410 is aligned in the die 110 via slots 115. The die 110 is positioned in the die assembly 100 via the hole 304 located in the first support 104. This will be discussed in detail later in the FIGS. 3A-3D.

Figure 1E:
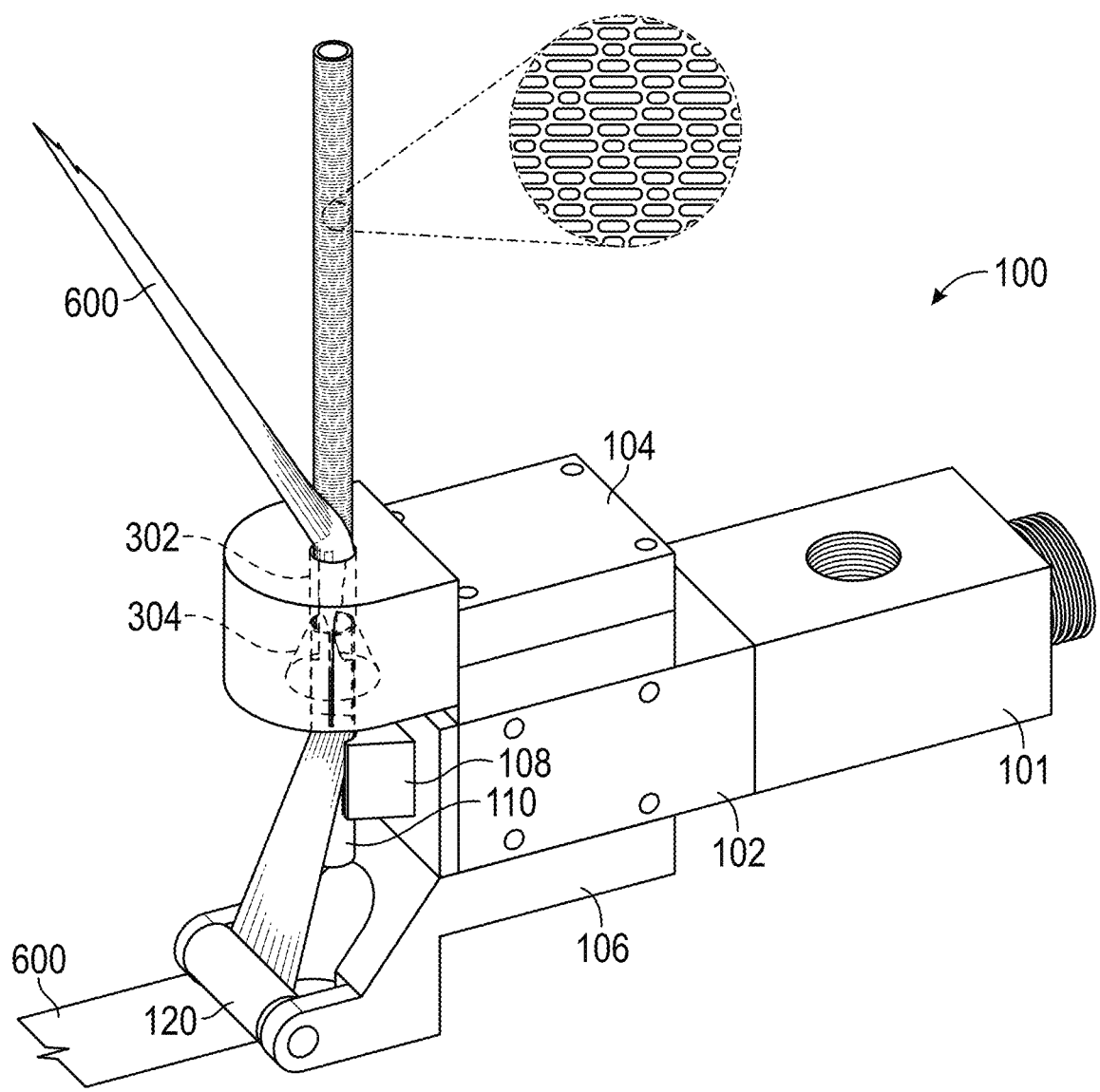
FIG. 1E is a perspective view of the die assembly with the template. It depicts the production of the textured conduit using the template and the die assembly.

FIG. 1E depicts the functioning of the die assembly 100 and the template 600 to produce a textured conduit 600. The manufacturing of a textured conduit is discussed in detail later.

Figure 2E:
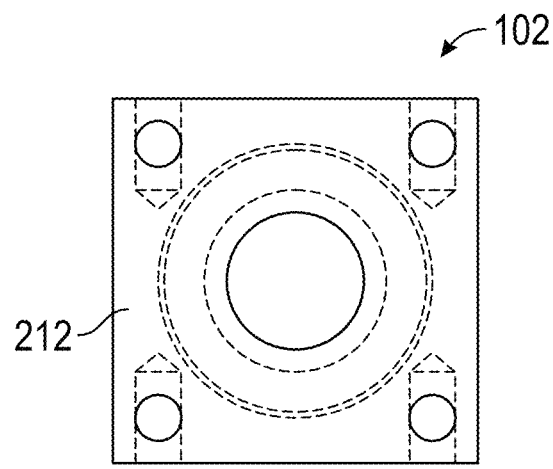
FIG. 2E represents a perspective view of the first attachment block.
Figure 2E:
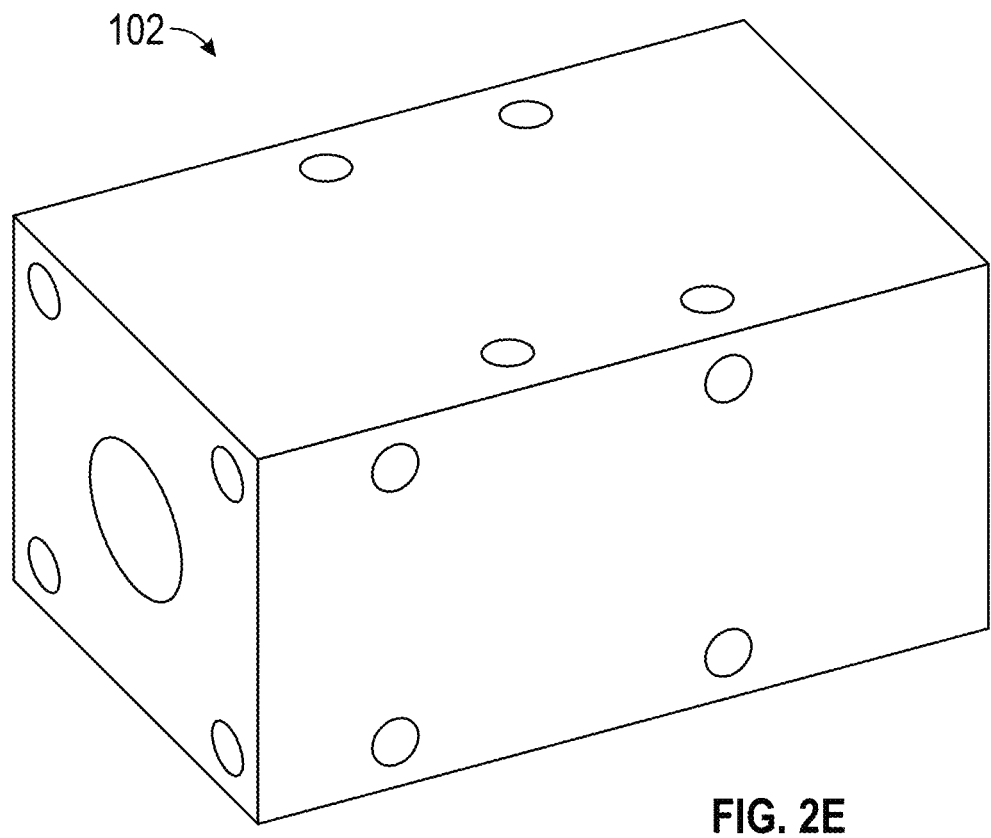

FIGS. 2A, 2B, 2C and 2D reflect different views the first attachment block 102. FIG. 2A depicts a side view of the first attachment block 102, while FIG. 2B depicts the top view of the same. FIG. 2C is a sectional view of the first attachment block 102 taken along section D-D of the FIG. 2A, while the FIG. 2D is a front view of the first attachment block 102 when viewed from the surface 212 that contacts the conduit 108. FIG. 2E represents a perspective view of the first attachment block 102.

With reference now to the FIG. 2A, the first attachment block 102 has an attachment portion 202 for attaching the first attachment block 102 to an extruder (not shown). The first attachment block 102 comprises a first face 201 that contacts the extruder and an opposing second face 212 that is in contact with conduit 108.

The first attachment portion 202 comprises threads and is disposed at the portion of the first attachment block 102 proximate to first face 201. In an embodiment, the attachment portion 202 comprises threads that enable the first attachment block 102 to be reversibly attached to the extruder. In another embodiment, the attachment portion 202 can comprise screws, bolts, nuts, and the like. An exemplary attachment portion 202 comprises threads.

The first attachment block 102 comprises a first passage 204 and a second passage 206 that is in fluid communication with the first passage 204. The second passage 206 has a smaller diameter than the first passage 204. The second passage 206 opens to second face 212. The second passage 206 is in fluid communication with a port contained in the conduit 108 that transfers the extrudate to a die 110. Molten or solvated polymeric material is discharged from the extruder (not shown) through the first passage and the second passage to the die 110 via the conduit 108. In an embodiment, the first and the second passages have circular cross-sectional areas, though other geometries such as square, rectangular, polygonal may also be used. The first attachment block 102 may have a plurality of screw holes 208 drilled in it to facilitate attachment to the first support 104 and the second support 106. In an embodiment, screw holes 208 may be used to reversibly attach the first support 104 and the second support 106 to the first attachment block 102. Holes 208 may be used to affix the optional strap 500 to the first attachment block 102. The first attachment block 102 comprises screw holes 209 that facilitate a reversible attachment with the conduit 108. Screws may be used to reversibly attach the first support 104, the second support 106 and the conduit 108 with the first attachment block 102.

Figure 3D:
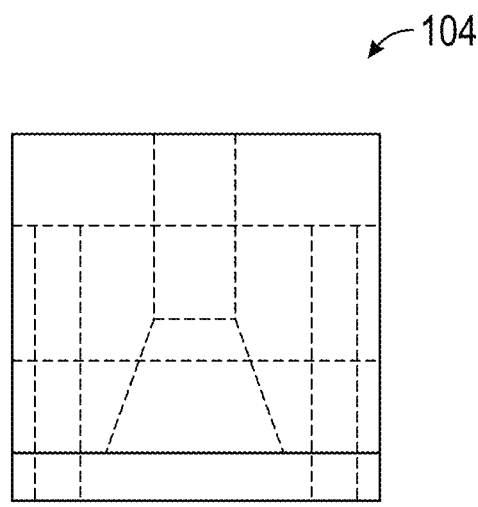
FIG. 3D depicts a perspective view of the first support.
Figure 3D:
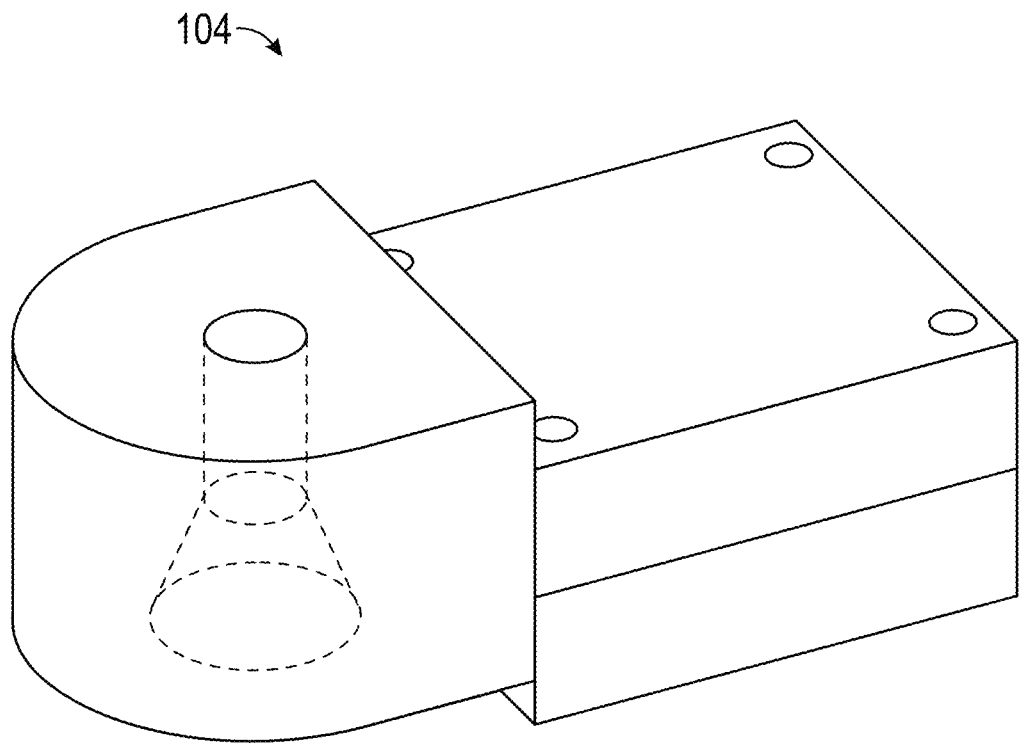

The FIGS. 3A, 3B and 3C depict the top view, the side view and the front view respectively of the first support 104. FIG. 3D depicts a perspective view of the first support 104. As can be seen in the FIG. 3A, the first support 104 comprises a plate 306 having two sections—a first section 305 and a second section 307. The first section 305 is the locating section and has screw holes 308 that facilitate reversibly attaching the first support 104 to the first attachment block 102. While screws (not shown) may be used to reversibly attach the first support 104 to the first attachment block 102, other attachment means such as nuts, rivets, welds, adhesives, and the like, may also be used to facilitate this attachment if so desired.

The second section 307 (as seen in the FIG. 3B) may have the same thickness as the first section 305, or alternatively, it may be thicker or thinner than the first section 305. In an exemplary embodiment, the second section 307 is thicker than the first section 305. The second section 307 has a first hole 302 and a second hole 304 for locating and supporting the die 110 during operation of the extruder. In an embodiment, the first hole 302 and the second hole 304 are concentric and share a common axis. In another embodiment, the second hole 304 is a conical hole that facilitates locating the die 110 in the first support 104.

In addition to serving as a locator for the die 110, the first hole 302 and the second hole 304 serve as guide tubes for facilitating contact between a template and the extruded article. The template (described later) contains a texture that is imprinted onto the extruded article by virtue of a compressive force (pressure) exerted by the guide tube onto the template and the extruded article as both the template and the extruded article travel through the holes 302 and 304.

Figure 4D:
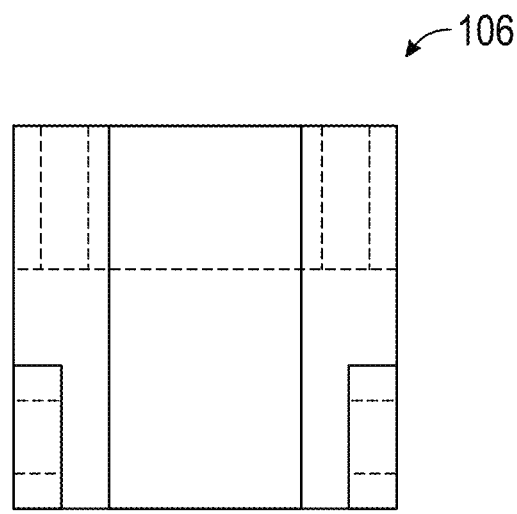
FIG. 4D depicts a perspective view of the second support with the feed roller affixed in position.
Figure 4D:
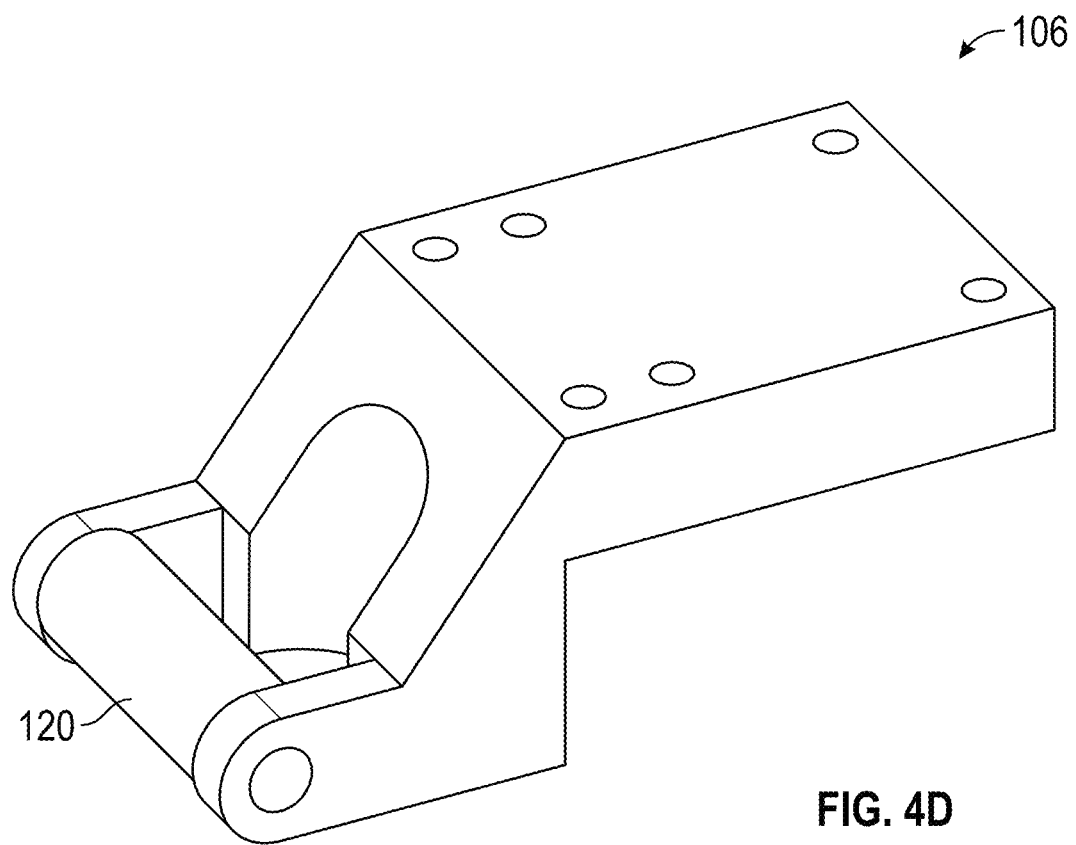

FIGS. 4A, 4B and 4C depict the top view, side view and front view respectively of the second support 106. FIG. 4D depicts a perspective view of the second support 106 with the feed roller 120 affixed in position. The second support 106 comprises a first section 320 that contains screw holes 308 for locating the second support 106 in the proper position on the first attachment block 102. The first section 320 is therefore the locating section and has screw holes 308 that facilitate reversibly attaching the second support 106 to the first attachment block 102. The second section 322 comprises arms 322A and 322B each of which have a hole 324 for locating the feed roller 120 (see FIG. 1B and see FIG. 4D). The axis of the feed roller shaft is concentric with the center line of the holes 324. The arms extend from the face 312 of the first attachment block 102 (see FIG. 2B) for a length effective to impart sufficient tension to a template to impart a texture to a surface of an extruded article that emanates from the die 110. This will be detailed later.

The feed roller 120 facilitates the movement of a template (not shown) towards the die 110 and the first section 104 (that contains holes 302 and 304 that serve as guide tubes for transferring texture).

The template 600 can be a single or multi-layer film. In an embodiment, the template is a multilayer film. The template generally comprises a first layer that has the texture to be imparted and a second layer that serves as a support. The second layer has a higher heat distortion temperature than the first layer. As may be seen in the FIG. 1E, the template 600 travels off of the feed roller 120 and contacts the outer surface of the die 110. The template 600 moves along the outer surface of the die 110 and contacts the extrudate as it emanates from the die. The textured surface of the template 600 is pressed against an outer surface of the extrudate by a guide tube 302 (detailed above in the FIG. 3B) to imprint the extrudate with the texture. The template travels with the same velocity as the extrudate in the same direction as the extrudate and during this travel, the template is pressed against the extrudate and transfers the texture to it. The texture is replicated on an entire surface of the extrudate along an entire length of the extrudate in a single pass of the extrudate through the guide tube.

Figure 5D:
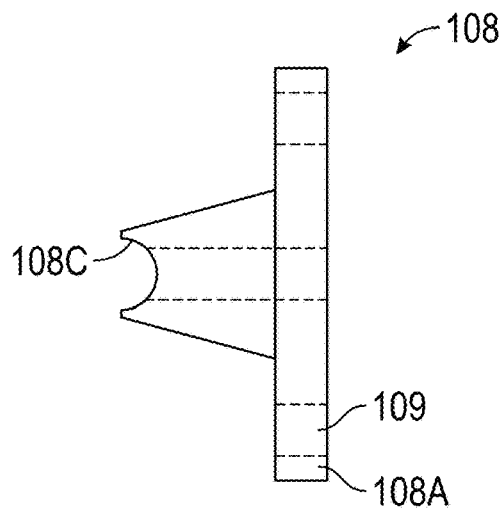
FIG. 5D is a depiction of a perspective view of the conduit that facilitates transmission of the molten polymer from the first attachment block to the die.
Figure 5D:
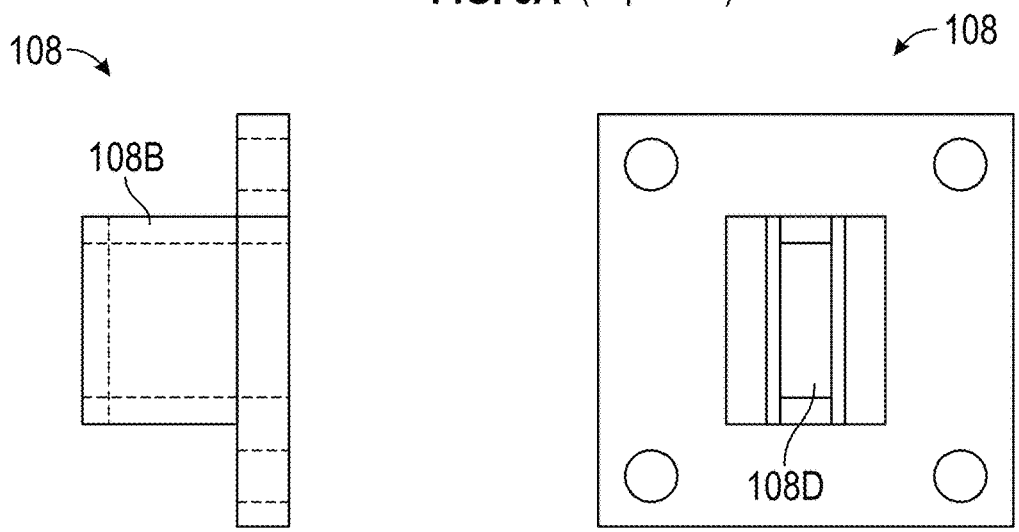
Figure 5D:
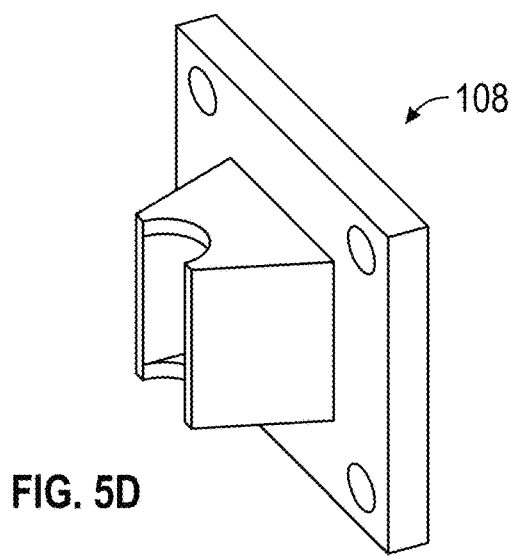

FIGS. 5A, 5B and 5C depict a top view, a side view and a front view respectively of the conduit 108. FIG. 5D is a depiction of a perspective view of the conduit 108. The conduit 108 serves to transport molten polymeric material from the first attachment block 102 to the die 110 and also serves to locate the die 110 and align it with the guide tube (formed by holes 302 and 304) located in the first support 104. FIG. 5A depicts the conduit 108 with a flange 108A that contacts surface 212 of the first attachment block 102. It contains screw holes 109 that facilitate a reversible attachment of the conduit 108 to the first attachment block 102. The conduit 108 comprises walls 108B that enclose a passage 108D through which the extrudate (molten polymeric material) flows from the extruder to the die. The walls 108B have a triangular section when viewed from the top and end in a locating element 108C that functions to locate the die 110 as depicted in the FIG. 1B. The passage 108D has an exit port that aligns with an entry port in the die, which is detailed below.

Figure 6E:
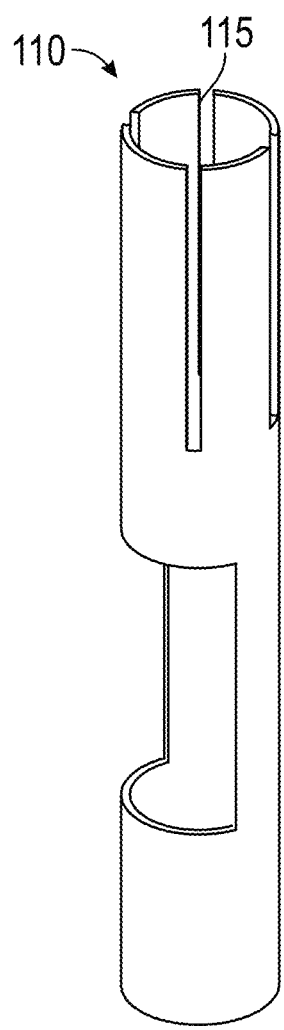
FIG. 6E depicts a perspective view of the die.
Figure 6F:
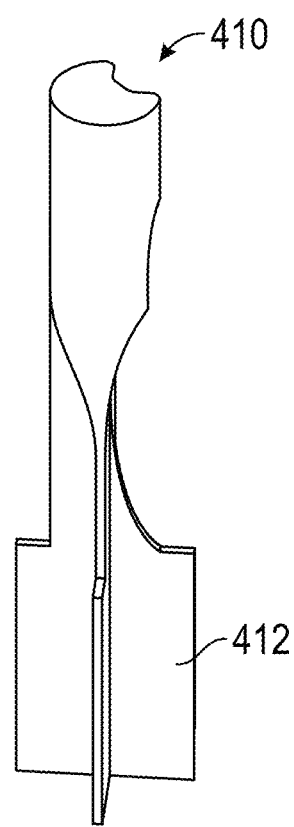
FIG. 6F depicts a perspective view of the extrusion pin. The extrusion pin has fins that fit into slots in the die.
Figure 7A:
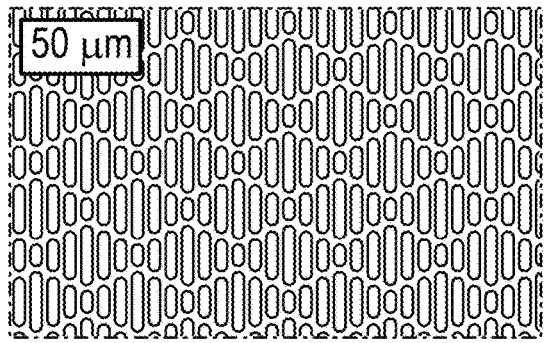
FIG. 7A depicts one texture that can be transferred from the travelling template to the conduit during the manufacturing process.
Figure 7B:
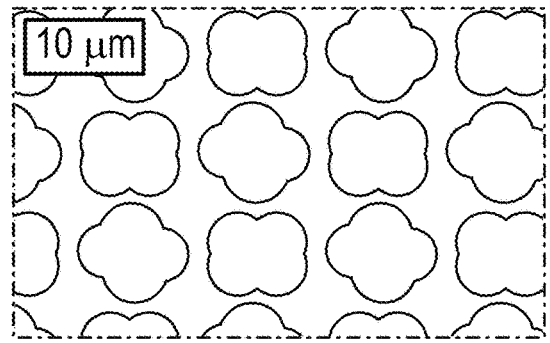
FIG. 7B depicts another texture that can be transferred from the travelling template to the conduit during the manufacturing process.
Figure 7C:
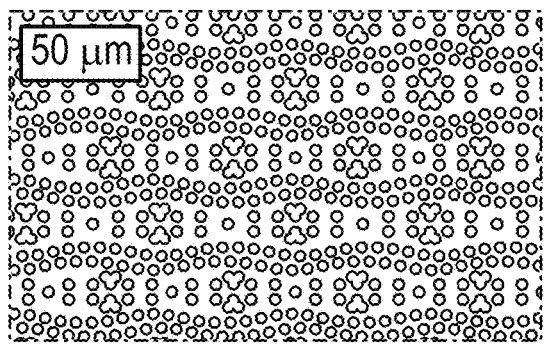
FIG. 7C depicts yet another texture that can be transferred from the travelling template to the conduit during the manufacturing process.
Figure 7D:
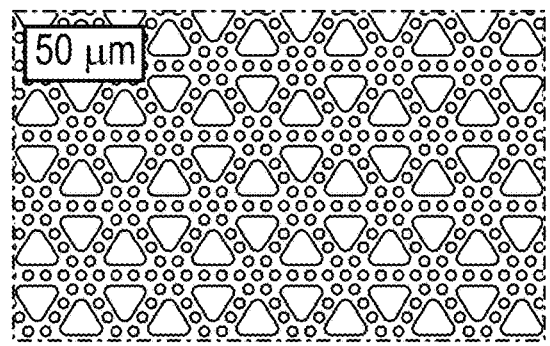
FIG. 7D depicts yet another texture that can be transferred from the travelling template to the conduit during the manufacturing process.

FIGS. 6A through 6E depict the die and the extrusion pin that floats in the die. FIG. 6A depicts a front and a side view of the die, while the FIG. 6B depicts a side view of the extrusion pin. FIG. 6C depicts another side view of the extrusion pin. FIG. 6D depicts two views of the extrusion pin in the die. FIG. 6E depicts a perspective view of the die 110. FIG. 6F depicts a perspective view of the extrusion pin 410. The extrusion pin 410 has fins 412 that fit into slots 115 in the die.

The die 110 as depicted in the FIGS. 6A and 6B comprises a first outer tube 110A with an entry port 110B. The entry port 110B is aligned with an exit port of the conduit 108 and serves to permit molten polymeric material discharged from the extruder to enter the die 110. The die contains a second tube 110C having a smaller diameter than the first outer tube 110A and that is located inside the outer tube 110A to provide for introducing a strip of radiopaque material into the wall of the extruded article. The second tube 110C may optionally extend below the bottom of the first outer tube 110A when mounted in the die assembly 100 and is affixed to the inner surface of the first outer tube 110A.

The first outer tube 110A has a first end 111 and a second end 113 that is opposed to the first end 111. The first end 111 receives an extrusion pin 410, which is detailed below. The second end 113 has an opening through which the second tube 110C may protrude as seen in the FIG. 6A. The second end 113 is sealed with a cap. The first outer tube 110A has slots 115 disposed in the portion above the entry port 110B. These slots 115 located in the perimeter of the first outer tube 110A enable the locating of the extrusion pin 410 by receiving fins 412 that are attached to the extrusion pin 410 (See FIG. 6C). This feature is described below in additional detail.

In an embodiment, at least one portion of the first outer tube 110A is slotted to receive the extrusion pin 410 (See FIG. 6C). The extrusion pin 410 comprises a post 414 that has one or more fins 412 that serve as locating elements for locating the extrusion pin 410 in the first outer tube 110A. The post 414 also has a passage in it that accommodates a third tube 416 that has a smaller diameter than the first outer tube 110A. The third tube 416 acts as a vent for the larger lumen (e.g., the urine lumen on the catheter). The extrusion pin 410 has a first end 413 and a second end 415 that is oppositely disposed to the first end 413. The fins 412 are located proximate to the first end 413, while the post 414 extends from the fins towards the second end 415. The post 414 has a different cross-sectional area at the point that it contacts the fins from the cross-sectional area at the second end 415. In an embodiment, the cross-sectional area at the second end 415 is greater than that at the point that it contacts the fins.

In an embodiment, the post 414 comprises a plurality of fins 412 that serve as locating elements for properly orienting the post 414 in the first outer tube 110A. FIG. 6B depicts one embodiment of the extrusion pin 410 that comprises 4 fins 412. The 4 fins are equally spaced on the perimeter of the post and protrude outwards from the post in the radial direction and appear to divide the post into 4 equal quadrants when viewed from the top. A molten polymer emanating from the extruder may be transported from the space in the first outer tube 110A below the fins to the space in the first outer tube 110A above the fins through the space between the post 414, the fins 412 and the tube 110A.

In the FIGS. 6B, 6D and 6F, it may be seen that the post 414 is not perfectly symmetrically distributed about the quadrants defined by the fins. The post 414 occupies a larger amount of cross-sectional area of three of the four quadrants (defined by the fins) when viewed from the top towards the fins. The cross-sectional area of the post 414 is equally distributed in three of the four quadrants and occupies a larger cross-sectional area of the three quadrants as compared with that of the fourth quadrant.

The area not occupied by the post in any of the quadrants may be used to accommodate one or more tubes such as the tube 110C depicted in the FIG. 6D. The tube 110C serves as the vent tube for the smaller lumen which is the inflation lumen in the finished catheter. These one or more tubes may be used for pressure equalization, for introducing materials into the walls of the extruded article or for introducing reactants to coat the inside of the tube as it is traverses the die 100.

While the post in the FIGS. 6D and 6F has a cross-sectional area that is crescent shaped (when viewed from the top), there is no restriction to the shape of the cross-sectional area and a multitude of different cross-sectional area post shapes may be employed. There is also no restriction on the number of tubes that may be contained in the first outer tube 110A. The post may comprise one or more passages (that may contain tubes) that permit pressure equalization in the extrudate to prevent it from collapsing or that are used for the introduction of fillers or strips of material into the extrudate. In an embodiment, when the extrudate is in the form of an elongated article, the passages may be used to deliver a radiopaque strip that is inserted into a wall of the article along its entire length.

In assembling the die 110, the fins 412 of the extrusion pin 410 (with second tube 110C welded thereto) are inserted into the slots in the first outer tube 110A as seen in the FIGS. 6D, 6E and 6F. The central axis of the extrusion pin may be concentric with the central axis of the first outer tube 110A. A third tube 416 (for pressure equalization) is inserted into the passage in the extrusion pin 410. The upper end of the first outer tube 110A is disposed in the guide tube (holes 302 and 304—see FIGS. 3A and 3B) of the first support 104. The second end 113 is open ended such that the tube 110C is open to the atmosphere to allow for pressure equilibration in the extruded article when it is formed.

An optional strap 500 shown in the FIG. 1 is applied to the die 110 to secure it to the conduit 108 and the first attachment block 102. The strap 500 is manufactured from a flexible material and is affixed by screws to the first attachment block 102. In an embodiment, the strap 500 is a belt that wraps around the die 110 and is secured under tension to the first attachment block 102. Both ends of the strap 500 are secured by screws to the first attachment block 102. The strap 500 may be manufactured from a flexible material such as a ductile metal, a polymer or a ceramic. It should be capable of withstanding the temperatures at which the extrusion is conducted and the temperatures that the die will be subjected to. In an embodiment, it can display dimensional stability to temperatures of greater than 250° C. (i.e., it does not begin to flow at temperatures of greater than or equal to about 250° C.)

Alternatively, the die 110 may be welded to the conduit 108, which in turn may be welded to the first attachment block 102. It is preferred to use the strap 500 to secure the die 110 to the conduit 108 and to the first attachment block 102.

In one embodiment, in one method of manufacturing the die assembly, the first attachment block 102 is affixed to the first support 104 and the second support 106 by screws. The screws are threaded into screw holes 208 (see FIGS. 1A, 1B, 1D and 1E). The conduit 108 is then affixed to the first attachment block 102 by screws via screw holes 209. The feed roller 120 is affixed to arms 322A and 322B of the second support 106. The die 110 (the outer tube 110A with the extrusion pin 410 disposed therein as shown in the FIG. 5A) is then positioned on the locating element 108C of the conduit 108. The end of the die 110 is located in the guide tube (the holes 302 and 304) of the first support 104. The optional strap 500 is then affixed to the first attachment block 102 in such a manner as to encompass the die 110 and to hold it in position along with the extrusion pin contained in the outer tube 110A.

In one embodiment as seen in the FIG. 1E, in one manner of operating the die assembly 100, the die assembly 100 is first affixed to the exit port of an extruder such that material emanating from the extruder (the extrudate) enters the inlet port 204 of the die assembly 100. The extruder may be a single screw extruder, a multiple screw extruder (e.g., a twin screw extruder), a piston extruder, or a Buss Kneader. A template 600 having the desired texture is then mounted around the feed roller 120. The extruder is started and the extrudate is transported through the die following which it is contacted with the template in the guide tube (holes 302 and 304).

The extrudate enters the die 100 at the entry port 110B and travels in the space between the fins, the post and the first outer tube 110A. After passing the fins on its travel upwards, the extrudate travels around the post towards the guide tube in the first support 104 where it contacts the template. Uniform pressure applied by the guide tube to the extrudate via the template causes a transfer of the texture to the extrudate before it exits the guide tube. In travelling around the post and the tube 110C, the extrudate develops passages that traverse the entire length of the extrudate. These passages may be used for transporting fluids from one end of the extrudate to the other. The template having imprinted its texture on the surface of the extrudate may be wound around another roller (not shown). FIGS. 7A through 7D show various textures that can be transferred from the travelling template to the conduit during the manufacturing process.

A textured surface of the template travels parallel to as surface the extrudate and imprints its texture on the extrudate when the two surfaces contact each other in the guide tube. The template wraps around the outer diameter of the extrudate and transfers its texture to the entire outer surface of the extrudate in a single pass through the guide tube. Once the wrapping process is started, the film cannot be bent away from the wrap. The die accommodates the straight path along the outer diameter of the product being extruded.

The die design is advantageous in that it has a removable extrusion pin that can be adjusted in the die tube 110 with positioning screws (not shown) and a side port (the second tube 110C) to allow secondary materials to be added to the tubing in the form of a barium stripe. The presence of a removable extrusion pin permits and easy replacement when it wears out. It also permits the use of different solid post sizes (with different cross-sectional areas) for manufacturing conduits having different inner diameters and different numbers of internal passages.

The die 110 has a novel design feature where the extrusion pin can be easily removed from the feed die secretion. Cleaning and changing extrusion pins can be completed without having to manufacture a new die. The pin section remains straight to aid in the fabrication of the feed section and venting through hypodermic tubing or similar. The pin is held in place by a stainless steel strap that presses it against the feed die section. The novel design includes the ability to introduce a flexible media (in the form of a template) into the high pressure zone of the die and wrap around the outer diameter of the shape being extruded. The die has a section of the die that is parallel to the outer diameter of the shape being extruded so that the template can be wrapped without buckling. Once the wrap is started the template cannot be bent away from the wrap.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:
1. A die assembly comprising:
a first attachment block having a passage, an inlet port and an exit port; where the passage is operative to transport a molten material from the inlet port to the exit port;
a die; and
a conduit; where the conduit comprises a passage that is operative to transport the molten material from the first attachment block to an entry port of the die; where the die comprises:
a first outer tube; and
an extrusion pin that comprises a post and fins; where the extrusion pin is located in the first outer tube using the fins and where the post extends from the fins in a direction away from the entry port of the die; and where the post comprises one or more passages; with at least one of these passages being open to an atmosphere to provide for pressure equalization; where the fins slide into and out of slots contained in the first outer tube; and
a travelling template; the travelling template being operative to contact an extrudate that emanates from the die and to transfer a texture to a surface of the extrudate by virtue of pressure applied by a guide tube to the extrudate via the travelling template.

2. The die assembly of claim 1, further comprising a first support that houses the guide tube; where the first support contacts an upper surface of the first attachment block.

3. The die assembly of claim 2, where the first support comprises a first hole and a second hole; where the first hole and the second hole are concentrically arranged and where the first hole facilitates locating the die and where the second hole acts as the guide tube.

4. The die assembly of claim 1, further comprising a second support that houses a feed roller; where the feed roller supplies the travelling template to contact the extrudate; and where the second support contacts the first attachment block at a surface that is opposed to the surface that contacts the first support.

5. The die assembly of claim 1, where the conduit contains a locating element at a surface that is opposed to a surface that contacts the first attachment block; where the locating elements facilitates a locating of the die.

6. The die assembly of claim 1, where an exit port in the passage of the conduit aligns itself with an entry port in the first outer tube.

7. The die assembly of claim 1, where the first outer tube comprises one or more tubes whose diameter is smaller than that of the first outer tube and where the one or more tubes are bonded to the first outer tube.

8. The die assembly of claim 7, where the bonding of the one or more tubes to the first outer tube is accomplished by welding.

9. The die assembly of claim 7, where the one or more tubes are operative to add a radiopaque stripe to the extrudate or to add a reactant to a surface of the extrudate.

10. The die assembly of claim 9, where the radiopaque stripe comprises barium.

11. The die assembly of claim 1, further comprising a strap that reversibly secures the die to the first attachment block.

12. The die assembly of claim 11, where the strap comprises a metal.

13. The die assembly of claim 12, where the extrusion pin can be inserted into the first outer tube and removed from the first outer tube.

14. The die assembly of claim 11, where the die is welded to the conduit and where the conduit is welded to the first attachment block.

15. The die assembly of claim 1, where the travelling template travels with a same velocity as the extrudate in a same direction as the extrudate.

16. The die assembly of claim 1, where the texture is replicated on an entire surface of the extrudate along an entire length of the extrudate in a single pass of the extrudate through the guide tube.

17. The die assembly of claim 1, where the die assembly is affixed to an outlet of an extruder.

18. A method comprising:
discharging to a die assembly an extrudate; where the die assembly comprises:
a first attachment block having a passage, an inlet port and an exit port; where the passage is operative to transport a molten material from the inlet port to the exit port;
a die; and
a conduit; where the conduit comprises a passage that is operative to transport the molten material from the first attachment block to an entry port of the die; where the die comprises:
a first outer tube; and
an extrusion pin that comprises a post and fins; where the extrusion pin is located in the first outer tube using the fins and where the post extends from the fins in a direction away from the entry port of the die; and where the post comprises one or more passages; with at least one of these passages being open to the atmosphere to provide for pressure equalization; where the fins slide into and out of slots contained in the first outer tube; and
a travelling template;
contacting the extrudate with the travelling template;
transferring a texture to a surface of the extrudate by virtue of pressure applied by a guide tube to the extrudate via the travelling template.

19. The method of claim 18, where the texture is transferred to an entire surface of the extrudate along its entire length in a single pass of the extrudate through the guide tube.

20. The method of claim 18, where the guide tube applies pressure to an entire surface area of a particular cross-section of the extrudate at any given time.

21. The method of claim 19, where the extrudate is a conduit.

* * * * *